United States Patent [19]

Zimmerman

[11] Patent Number: 4,937,444
[45] Date of Patent: Jun. 26, 1990

[54] OPTICAL FLEX SENSOR

[75] Inventor: Thomas G. Zimmerman, Flushing, N.Y.

[73] Assignee: VPL Research, Inc., Redwood City, Calif.

[21] Appl. No.: 418,919

[22] Filed: Oct. 5, 1989

Related U.S. Application Data

[60] Continuation of Ser. No. 218,426, Jul. 8, 1988, abandoned, which is a continuation of Ser. No. 892,888, Jul. 29, 1986, abandoned, which is a continuation of Ser. No. 745,035, Aug. 1, 1985, abandoned, which is a division of Ser. No. 428,322, Sep. 29, 1982, Pat. No. 4,542,291.

[51] Int. Cl.$^5$ ............................................. G01D 5/34
[52] U.S. Cl. .................... 250/231.1; 250/221; 341/31
[58] Field of Search ............... 250/226, 231 R, 551, 250/221, 227; 341/31; 73/293, 760, 788, 800, 862; 455/602

[56] References Cited

U.S. PATENT DOCUMENTS

| | | | |
|---|---|---|---|
| 1,335,272 | 3/1920 | Broughton | 340/321 |
| 2,356,267 | 8/1944 | Pelunis | 73/293 |
| 3,510,210 | 5/1970 | Haney | 352/39 |
| 3,777,086 | 12/1973 | Riedo | 200/52 R |
| 4,059,830 | 11/1977 | Threadgill | 340/279 |
| 4,074,444 | 2/1988 | Laenger | 35/35 A |
| 4,209,255 | 6/1980 | Heynau | 250/203 R |
| 4,302,138 | 11/1981 | Zarudiansky | 414/5 |
| 4,355,805 | 10/1982 | Baer et al. | 273/313 |
| 4,408,495 | 10/1983 | Couch | 250/227 |
| 4,414,537 | 11/1983 | Grimes | 340/365 R |
| 4,414,984 | 11/1983 | Zarudiansky | 128/774 |
| 4,444,205 | 4/1984 | Jackson | 128/782 |
| 4,524,348 | 6/1985 | Lefkowitz | 340/365 R |

OTHER PUBLICATIONS

"One-Point Touch Input of Vector Information for Computer Displays" C. Herot and G. Weinzapfel, *Computer Graphics*, vol. 12, No. 3, Aug. 1978.

"Digital Actuator Utilizing Shape Memory Effect", Honma, et al. lecture given at 30th Anniversary of TOKAI Branch foundation on Jul. 14, 1981.

*Primary Examiner*—David C. Nelms
*Attorney, Agent, or Firm*—Townsend and Townsend

[57] ABSTRACT

An optical flex sensor is provided and consists of a flexible tube having two ends, a reflective interior wall within the flexible tube and a light source placed within one end of the flexible tube and a photosensitive detector placed within the other end of the flexible tube to detect a combination of direct light rays and reflected rays when the flexible tube is bent.

22 Claims, 1 Drawing Sheet

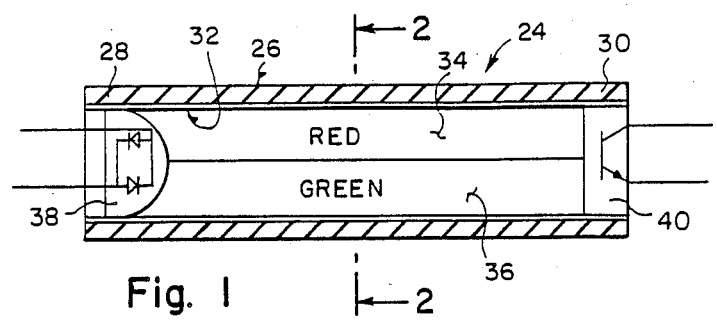
Fig. 1
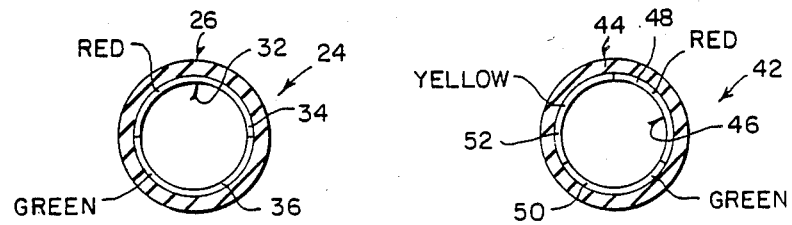
Fig. 2  Fig. 2A
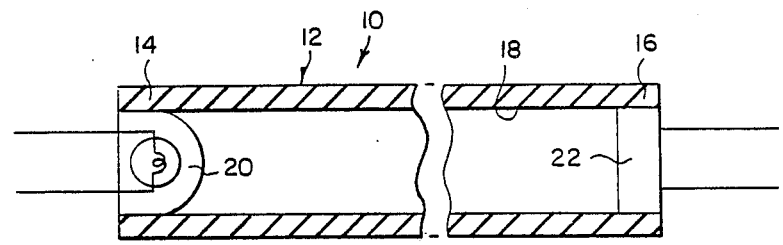
Fig. 3
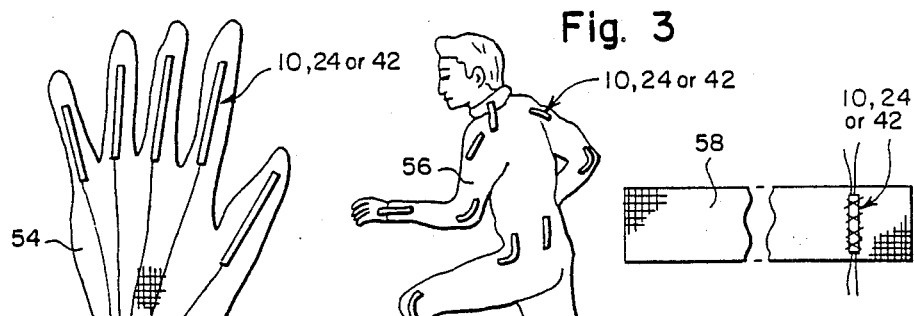
Fig. 4
Fig. 5
Fig. 6

OPTICAL FLEX SENSOR

This is a continuation of Ser. No. 07/218,426, filed July 8, 1988, now abandoned, which is a continuation of Ser. No. 06/892,888, filed July 29, 1986, now abandoned, which is a continuation of Ser. No. 06/745,035, filed Aug. 1, 1985, now abandoned, which is a division of Ser. No. 06/428,322, filed Sept. 29, 1982, which is now U.S. Pat. No. 4,542,291, issued Sept. 17, 1985.

BACKGROUND OF THE INVENTION

The instant invention relates generally to position detectors and more specifically it relates to an optical flex sensor that produces an output signal in response to bending.

SUMMARY OF THE INVENTION

A principal object of the present invention is to provide output signals correlating to the position of corresponding joints.

Another object is to provide an optical flex sensor that is simple, rugged, small and lightweight permitting unhindered, comfortable and natural movement.

An additional object is to provide an optical flex sensor having electrical components that are hermetically sealed making them waterproof and resistant to environmental contaminants.

A further object is to provide an optical flex sensor that uses inexpensive common materials and is assembled either by hand or with simple tools.

A still further object is to provide an optical flex sensor that can be made in a variety of diameters, lengths, materials, and with electrical components that utilize low current and voltage making them safe to use.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The figures in the drawings are briefly described as follows:

FIG. 1 is a longitudinal cross sectional view of the invention.

FIG. 2 is a cross sectional view taken along line 2—2 in FIG. 1.

FIG. 2A is a cross sectional view similar to FIG. 2 illustrating another embodiment of the invention.

FIG. 3 is a cross sectional view of still another embodiment of the invention.

FIG. 4 is a plan view of a glove embodiment of the invention.

FIG. 5 is a perspective view of a body suit embodiment of the invention.

FIG. 6 is a plan view of a elastic bandage embodiment of the invention.

DESCRIPTION OF THE PREFERRED EMBODIMENT

Turning now descriptively to the drawings, in which similar reference characters denote similar elements throughout the several views, FIG. 3 illustrates an optical flex sensor 10. The sensor 10 consists of a flexible tube 12 that has open ends 14 and 16 a reflective interior wall 18 within the flexible tube 12, a light source 20 placed within end 14 of the flexible tube 12 and a photosensitive detector, or light transmitting device such as an optical fiber 22 is placed within end 16 of the flexible tube 12 so that the intensity of a combination of direct light rays and reflected rays may be detected when the flexible tube 12 is bent.

The flexible tube 10 may be made of black rubber or other suitable material while the interior wall 18 may be coated with aluminum spray paint or other suitable material or in some instants even left untreated.

In its unflexed position the tube 12 is straight. In this position the light emitted from the light source 20 strikes the photosensitive detector 22. As the tube 12 is bent the light received is a combination of direct light rays and reflected rays. The amount of light, reaching the photosensitive detector 22 decreases until a position is reached in which all the light reaching the detector 22 is reflected.

The nature of the photosensitive detector 22 is to change its resistance with light intensity. The combined effect of the bent tube 12 on the light path and the photosensitivity of the detector produces a device that changes its electrical resistance when flexed.

It is to be further appreciated that detector 22 may be a phototransistor, photo silicon controlled rectifier, a photocell, or in the broad sense an optical fiber which carrie the signal to another location, or any other of various components which has some output parameter which changes in response to light intensity.

FIGS. 1 and 2 show another embodiment of an optical flex sensor 24. The sensor 24 consists of a flexible tube 26 that has two ends 28 and 30, a reflective interior wall 32 made out of two different longitudinal color areas red 34 and green 36 within the flexible tube 26, a light source 38 that may be either light emitting diodes or infrared emitters and a photosensitive detector 40 that is a silicon phototransistor.

FIG. 2A shows another embodiment of an optical flex sensor 42. This sensor has within the flexible tube 44 a reflective interior wall 46 made out of three different longitudinal color areas red 40, green 50 and yellow 52. The two different color areas 34 and 36 in the sensor 24 and the three different color areas 40, 50 and 52 in the sensor 42 cause the intensity of light which reaches the photosensitive detector 40 at the opposite end of the tube to be modified according to whether a light source of similar color or different color is reflected from this surface.

In these embodiment the light source 38 would consist of the same multiple number of similar colored sources as there are color wall areas on wall 46 of tube 44. These multiple sources would be pulsed on and off at various interval of time and the output parameter of detector 40 would accordingly be corresponding sampled during these time intervals. In this manner the information present would allow one to determine not only the degree that the device is bent but also a direction of bending. It is to be appreciated that the accuracy obtainable of the direction in which the device is bent is increased when a larger number of multiple colored light sources an correspondingly colored walls are employed. Although only the specific case of one, two, and three colors are illustrated in the accompany drawings any number could be chosen and ten for instant would not be inconceivable number and certainly would permit determining this bending direction with a much higher degree of resolution than three colors would.

In the same way that there is a larger number of suitable photodetector devices which can be utilized for elements 40, and 22, there are also a large variety of light sources which are suitable for element 38, and 20 not to mention just a few such as light emitting diodes, incandescent lamps, in the broad sense an optical fiber carrying light from another source, neon lamps, and other gaseous sources etc.

The sensors 10, 24 or 42 can be attached to a fabric of a glove 54 (see FIG. 4), a body suit 56 (see FIG. 5) or an elastic bandage 58 (see FIG. 6) to be placed on appendages of a being or creature to electrically measure the position of joints and limbs, or at least obtain information about there position, velocity, acceleration, etc. or other related parameters.

It is to be further appreciated that sensors 10, 24, and 42 can have their information outputs, and their light source inputs connected by an appropriate network of electrical wires or fiber optical paths (not shown) as required by other design considerations.

The means for securing these sensor into may be quite varied depending on their related application they might be sewn, cemented, or other wise inserted in various prexisting tubes etc. Signals from these sensors can be processed for application in kinesiology, physical therapy, computer animation, remote control and man to man machine interface. The optical flex sensors can be used as digital (on/off) or analog switches. The optical flex sensors 10, 24 or 42 may also be used to indicate the bend of mechanical joints or inclination of platforms, as well as a host of other applications to numerous to mention.

While certain novel features of this invention have been shown and described and are pointed out in the annexed claims, it will be understood that various omissions, substitutions and changes in the forms and details of the device illustrated and in its operation can be made by those skilled in the art with out departing from the spirit of the invention.

What is claimed is:

1. An optical flex sensor which comprises:
   (a) a flexible tube having two ends;
   (b) a light reflective material coated on the interior wall within said flexible tube;
   (c) at least one light source placed within a first end of said flexible tube; and
   (d) a photosensitive detector placed within a second end of said flexible tube to detect the intensity of a light ray impinging on said photosensitive detector when said flexible tube is bent, said detector providing a signal which varies according to the continuous extent of flexing of said tube.
2. An optical flex sensor as recited in claim 1 wherein said flexible tube is made of rubber.
3. An optical flex sensor as recited in claim 2 wherein the reflective interior wall is coated with at least one reflective material.
4. An optical flex sensor as recited in claim 3 wherein said photosensitive detector includes a silicon phototransistor.
5. An optical flex sensor as recited in claim 4 wherein said light source includes at least one light emitting diode.
6. An optical flex sensor as recited in claim 5 wherein the light source and detector include optical fibers.
7. An optical flex sensor as recited in claim 4 wherein the reflective interior wall is coated with a plurality of differently colored light reflective materials on longitudinally separate areas, further including a plurality of light sources having colors corresponding to the colors of the light reflective materials.
8. The sensor according to claim 1 wherein the detector further comprises resistance means for producing a resistance which continuously varies as the flexible tube is bent, the resistance corresponding to the degree of bending of the flexible tube.
9. An optical flex sensor comprising:
   a flexible tube having two ends and an interior wall, said interior wall being coated with a plurality of differently colored light reflective materials on longitudinally separate areas;
   a plurality of light sources at a first end of the flexible tube having colors corresponding to the colors of the light reflective materials; and
   a photosensitive detector at a second end of the flexible tube capable of detecting the light emitted from the plurality of light reflective sources.
10. An optical flex sensor as in claim 9, wherein the flexible tube is made of rubber.
11. An optical flex sensor as in claim 9, wherein the light sources and detectors include optical fibers.
12. An optical flex sensor as in claim 11, wherein the photosensitive detector includes a silicon phototransistor.
13. An optical flex sensor as in claim 11, wherein the light sources include light emitting diodes.
14. A flex sensor comprising:
    a light source;
    a light sensor;
    a flexible conduit for communicating light from the light source to the light sensor as the conduit is bent in a selected direction, the conduit including means for decreasing the amount of light communicated from the light source to the light sensor as the conduit is bent; and
    wherein the light sensor includes means for providing a signal corresponding to the continuous amount of light received by the sensor as the conduit is bent.
15. The sensor according to claim 14 wherein the conduit comprises a flexible tube.
16. The sensor according to claim 14 wherein the light sensor further comprises resistance means for producing a resistance which continuously varies as the flexible conduit is bent, the resistance corresponding to the degree of bending of the flexible conduit.
17. A method of indicating flexure comprising the steps of:
    disposing a flexible conduit between a light source and a light sensor;
    bending the conduit;
    communicating light from the light source to the light sensor as the conduit is being bent;
    decreasing the amount of light received by the light sensor as the conduit is being bent;
    providing a signal corresponding to the continuous amount of light received by the light sensor; and
    indicating the continuous extent of bending of the conduit with the signal.
18. The method according to claim 17 wherein the signal providing step comprises the step of providing a resistance which varies according to the amount of light received by the sensor.

19. The method according to claim 18 wherein the conduit disposing step further comprises the step of disposing a tube between the light source and the light sensor.

20. The method according to claim 19 further comprising the step of coating an interior wall of the tube with a reflective material.

21. The method according to claim 20 wherein the coating step further comprises the step of coating the interior wall of the tube with a plurality of differently colored light reflective materials on longitudinally separate area of the tube.

22. The method according to claim 21 further comprising the step of disposing a plurality of the light sources at one end of the tube, the plurality of light sources having colors corresponding to the colors of the light reflective material.

* * * * *